US006965053B2

(12) United States Patent
Forlin et al.

(10) Patent No.: US 6,965,053 B2
(45) Date of Patent: Nov. 15, 2005

(54) PROCESS FOR THE PRODUCTION OF AROMATIC AMINES

(75) Inventors: Anna Forlin, Vigonza (IT); Antonio Beccari, I-Caorle (IT)

(73) Assignee: Dow Global Technologies Inc., Midland, MI (US)

( * ) Notice: Subject to any disclaimer, the term of this patent is extended or adjusted under 35 U.S.C. 154(b) by 188 days.

(21) Appl. No.: 10/312,349

(22) PCT Filed: Jun. 29, 2001

(86) PCT No.: PCT/EP01/07478

§ 371 (c)(1),
(2), (4) Date: Jul. 7, 2003

(87) PCT Pub. No.: WO02/00598

PCT Pub. Date: Jan. 3, 2002

(65) Prior Publication Data

US 2004/0092773 A1     May 13, 2004

(30) Foreign Application Priority Data

Jun. 29, 2000    (IT)    .................... MI2000A1457

(51) Int. Cl.$^7$ ............................................. C07C 209/36
(52) U.S. Cl. ................... 564/423; 564/420; 564/421; 564/422
(58) Field of Search ........................ 564/423

(56) References Cited

U.S. PATENT DOCUMENTS 5,563,296 A * 10/1996 Zarnack et al. ............. 564/422

FOREIGN PATENT DOCUMENTS

DE           198 57 409 A    *  6/2002    ........... C07B 43/04

* cited by examiner

Primary Examiner—Brian Davis

(57) ABSTRACT

A process for the production of aromatic amines which comprises the reduction of an aromatic compound containing at least two nitro groups with hydrogen in the presence of a catalyst is disclosed. The reaction is carried out so as to maintain up to 10% by weight of reaction intermediates (aminonitrites) and the solution produced is treated to recover the aromatic amine with a purity of over 99% and a mixture consisting of aromatic amine and reaction intermediates is recycled to the reactor.

16 Claims, No Drawings

PROCESS FOR THE PRODUCTION OF AROMATIC AMINES

The present application is a National Phase filing of the International Application No. PCT/EP01/07478 with a filing date of 29 Jun. 2001, which claims priority to Italian Application MI2000A001457 filed 29 Jun. 2000.

This invention relates to a process for the production of an aromatic amine. More specifically, the invention relates to a continuous process for the production of an aromatic diamine, especially metatoluenediamine.

Processes for producing aromatic amines by the hydrogenation of the corresponding nitro-compounds are known for example from DE 1,542,544, BE 631,964, FR 1,359,438, GB 768,111, and U.S. Pat. Nos. 3,935,264, 4,387,247, 4,717,774, 5,563,296, 5,728,880 and 5,849,947.

According to these processes, aromatic derivatives containing two or more nitro groups are reacted with hydrogen, or another reducing gas such as hydrogen sulfide, at a high temperature and under pressure in the presence of catalysts selected from heavy transition metals such as iron, cobalt, nickel, copper, silver or caesium, used as such, on inert carriers, or in the form of oxides, hydroxides or carbonates. The reaction may be carried out in the presence of solvents, generally water, aliphatic alcohols or their mixtures, and, optionally, in the presence of reduction adjuvants of the nitro group to the amine group such as carbon monoxide. The reaction is generally carried out in stirred reactors where the catalyst, in a finely subdivided form, is kept in suspension and is extracted in continuous fashion together with the amines produced.

A drawback of at least some of these processes for producing aromatic di- or poly-amines, such as metatoluenediamine, is that they produce an end-product in which there are numerous reaction by-products which are also formed as a result of the operating conditions of the reactors, in particular high temperature and pressure. These reaction by-products, as well as reducing the yield to useful product, also pollute the desired product. The lack of purity of the product is undesirable with regard to downstream processing and may have a serious effect on the running of production plants.

U.S. Pat. No. 5,563,296 discloses a process for the production of aromatic amines which, although carried out at a high temperature, generally between 120 and 220° C., is said to significantly reduce the formation of secondary reactions. This process comprises feeding an aromatic compound containing two or more nitro groups, hydrogen and the catalyst to a "Jet Loop" type reactor where the mixing effect is guaranteed by a Venturi tube whose diffuser is immersed in the reagent suspension. The latter, in turn, is continuously extracted by means of a pump and is partially recycled to the Venturi tube as a device for sucking the reagents and mixing them with the catalyst dispersed in the suspension. The suspension extracted from the bottom of the reactor is cooled in a heat exchanger outside the reaction container, before being recycled to the Venturi tube, to eliminate the reaction heat.

The Applicant has now found a process for the preparation of an aromatic amine which, without the necessity of having to resort to particular types of reactor, as in the case of the process disclosed in U.S. Pat. No. 5,563,296, allows a product to be recovered from a traditional reaction container having a high level of purity.

The object of the present invention therefore relates to a process for the production of an aromatic amine which comprises:

a) feeding an aromatic compound having at least two nitro groups to a reaction zone and contacting the compound with a catalyst;

b) passing, preferably in a continuous stream, a reducing gas through the reaction zone to contact the gas with the said compound;

c) reducing the nitro groups into amine groups in the presence of the catalyst, the catalyst comprising a supported active metal, until a conversion degree is reached at which the level of reaction intermediates is 30% or less by weight of the aromatic amine, preferably 10% or less, for example from 5 to 10%;

d) discharging a first stream from the reaction zone and recycling the first stream to the reaction zone;

e) discharging a second stream comprising the desired aromatic amine product and 30% or less, preferably 10% or less, for example from 5 to 10% by weight based on the aromatic amine of reaction intermediates from the reaction zone;

f) recovering from the stream of step (e) the aromatic amine at a purity of over 99% and a mixture containing at least 50% of aromatic amine and up to 50% by weight of reaction intermediates; and g) feeding the mixture of step (f) to the reaction zone.

Preferably, the process of the invention is continuous.

Suitably, the reaction zone is defined by a reaction container equipped with means to agitate the components in the reaction zone, for example a stirrer.

Desirably, the first stream is discharged from the bottom of the reaction zone. The first reaction stream is suitably recycled to the reaction zone by means of a continuous, closed recycle loop. Prior to re-entering the reaction zone, heat is preferably removed from the first stream by heat exchange so as to regulate the temperature in the reaction zone.

The catalyst may be in any suitable form for contact with the aromatic compound to catalyze reduction of the compound but is preferably finely divided, more preferably finely sub-divided.

In a preferred embodiment, the catalyst is in the form of a suspension comprising a finely subdivided catalyst dispersed in a reaction medium. Preferably the reaction medium comprises water. Suitably, the reducing gas is bubbled through the suspension and contacted with the aromatic compound.

Preferably, in step e) of the process of the invention, the second stream is removed from the reaction zone by means of a filter cartridge immersed in the suspension comprising the catalyst.

The reducing gas suitably comprises hydrogen and in a preferred embodiment is substantially pure hydrogen.

The intermediate produced during the reduction reaction is typically an aminonitrite, that is a compound that has only been partly reduced from the aromatic reagent.

The process for the production of an aromatic amine of the present invention is particularly suitable for the production of metatoluenediamine starting from dinitrotoluene. In this case, a stirred reactor (CSTR) or a column reactor fed at the head with the dinitrotoluene reagent and at the bottom with the reducing gas by means of a micro-bubble diffuser may be employed as desired. In such a column reactor in a reaction medium the reagents contact in a countercurrent manner with the reagent descending slowly owing to the micro-bubbles of the reducing gas which are rising, and the reducing gas itself.

In the case of dinitrotoluene, during the reaction, the dinitrotolu n is first reduced to amino-nitrotoluene. In the case of 2,4-dinitrotoluene, the intermediate comprises 4-amino-2-nitrotoluene and 2-amino-4-nitrotoluene isomers then to metatoluenediamine. To obtain a partially reduced product, it is preferable to operate with molar ratios of reducing gas to aromatic compound, for example, hydrogen/dinitrotoluene from 5 to 10.

Suitably, the suspension discharged from the bottom of the reaction container is practically without high-boiling by-products. It is preferably continuously extracted, for example by means of a pump capable of processing a suspension, subjected to cooling in a heat exchanger to eliminate or reduce the reaction heat, and subsequently recycled to the reactor. The recycling operation advantageously enables the temperature to be regulated inside the reactor and also favours the homogenization of the suspension and therefore effects a better contact between the reagents and catalyst.

In addition to the reduction of dinitrotoluene to metatoluenediamine, the present process is also suitable for the reduction of other aromatic compounds containing nitro groups such as dinitrobenzene, and its corresponding isomers, and dinitroxylenes.

Any catalyst capable of catalyzing the reduction of nitro groups to amine groups can be used in the process of the present invention. Examples of catalysts which are particularly suitable for the purpose are metals belonging to group VIII of the Periodic Table such as iron, nickel, cobalt, ruthenium, palladium and platinum. Preferably the catalyst is supported on an inert material such as alumina or silica. The especially preferred catalyst according to the present invention is palladium supported on carbon.

The catalyst suitably is in the form of particles with an average dimension from 10 to 100 $\mu$m. The catalyst desirably contains the Group VIII metal, for example palladium, at a level from 0.5 to 20% w/w, with respect to the total weight of the catalyst.

Suitably, the recycling flow-rate of the first stream in step (d), and its temperature are regulated so as to maintain a temperature from 120 to 220° C. in the reaction zone. The pressure inside the reaction zone is suitably from 0.1 to 10 MPa and preferably from 0.1 to 5 MPa.

The second stream is preferably fed to a system for the recovery of the aromatic amine, for example to a distillation process, preferably a distillation column under vacuum. To avoid or reduce the formation of heavy products, the distillation process suitably is operated under vacuum, at a pressure from 10 to 20 mmHg and at a temperature, at the bottom in the case of a column, of 150 to 160° C.

As an alternative to distillation, the process of the present invention may comprise feeding the second stream discharged from the reaction zone to a crystallization unit where the aromatic amine is crystallized, for example at a temperature of 90 to 110° C. and is subsequently recovered in a manner known to those skilled in the art. In both cases, distillation under vacuum and crystallization, the remaining mixture containing at least 50% of aromatic amine and up to 50% by weight of reaction intermediates, preferably 50/50 is recycled to the reaction zone.

The invention is illustrated by the following non-limiting examples.

EXAMPLE 1

18,000 kg/h of 2,4-dinitrotoluene was fed to the upper part of a CSTR stirred reaction container having a volume of 30 m$^3$, and 1,187 kg/h of hydrogen was fed close to the bottom, by means of a bubble distributor.

An aqueous suspension containing 1% by weight of solid catalyst consisting of carbon particles on which 5% by weight of palladium is distributed was inside the reactor. The particles of catalyst had an average dimension of 30 $\mu$m and a surface area of 900 m$^2$/g.

A temperature of 135° C. and a pressure of 0.4 MPa was maintained inside the reactor.

90 m$^3$/h of suspension was discharged from the bottom of the reactor, cooled in an external reactor to 90° C. and recycled to the head of the reactor. An aqueous solution containing 90% of 2,4-toluenediamine (TDA) and 10% of 2-amino-4-nitrotoluene (AMN) was extracted by means of filter cartridges immersed in the suspension and was fed to a distillation column operating at 10 mmHg and at a temperature of 150° C. at the bottom.

11.945 Kg/h of 2,4-toluenediamine (TDA), having a purity of over 99%, was discharged from the head of the column, and an aqueous solution containing AMN and TDA (50/50) from the bottom, which was recycled to the reactor.

EXAMPLE 2

The aqueous solution extracted by means of the filter cartridges of the reactor as per Example 1, having a composition of 90% of TDA, 8% of AMN and 2% of water, was fed to a static drop film crystallizer operating at a temperature of about 90 to 110° C.

The feed (10 parts) to the crystallizer was separated into 8 parts of TDA and 2 parts of a mixture of TDA, AMN and water recycled to the reactor. To reach a purity of over 99%, the crystallized product (TDA) was washed with 1 part of water, also recycled to the reactor.

What is claimed is:

1. A process for the production of an aromatic amine which comprises:
   a) feeding an aromatic compound having at least two nitro groups to a reaction zone and contacting the compound with a catalyst, wherein the catalyst is in the form of a suspension within the reaction zone;
   b) passing a reducing gas through the reaction zone to contact the gas with the said compound;
   c) reducing the nitro groups into amine groups in the presence of the catalyst, the catalyst comprising a supported active metal, until a conversion degree is reached at which the level of reaction intermediates is 30% or less by weight of the aromatic amine;
   d) discharging a first stream from the reaction zone and recycling the first stream to the reaction zone;
   e) discharging a second stream comprising the desired aromatic amine product and 30% or less by weight based on the aromatic amine of reaction intermediates from the reaction zone;
   f) recovering from the stream of step (e) the aromatic amine at a purity of over 99% and a mixture containing at least 50% of aromatic amine and up to 50% by weight of reaction intermediates; and
   g) feeding the mixture of step (f) to the reaction zone.

2. A process according to claim 1 which is continuous and in which the level of the reaction intermediate in step c) and e) is 10% or less.

3. A process according to claim 1 in which heat is removed from the first stream by heat exchange so as to regulate the temperature in the reaction zone.

4. The process according to claim 1 in which the catalyst is finely divided.

5. A process according to claim 4 in which the catalyst is in the form of a suspension comprising a finely divided catalyst dispersed in a reaction medium.

6. A process according to claim 5 in which the reaction medium comprises water.

7. A process according to claim 5 in which the reducing gas is bubbled through the suspension and contacted with the aromatic compound and, in step e), the second stream is removed from the reaction zone by means of a filter cartridge immersed in the suspension comprising the catalyst.

8. A process according to claim 7 in which the reducing gas comprises hydrogen.

9. A process according to claim 1 in which the aromatic compound containing at least two nitro groups is dinitrotoluene.

10. A process according to claim 1 in which the molar ratios of reducing gas to aromatic compound is from 5:1 to 10:1.

11. A process according to claim 1 in which the catalyst is selected from metals belonging to group VIII of the Periodic Table.

12. A process according to claim 11 in which the catalyst is palladium supported on carbon.

13. A process according to claim 12 in which the catalyst is in the form of particles with an average dimension from 10 to 100 $\mu$m.

14. A process according to claim 1 in which the temperature in the reaction zone is from 120 to 220° C. and the pressure is from 0.5 to 10 MPa.

15. A process according to claim 1 in which the second stream is fed to a distillation process for the recovery of the aromatic amine.

16. A process according to claim 15 in which the second stream discharged from the reaction zone is fed to a crystallization unit from which the aromatic amine is recovered.

* * * * *